US 6,770,275 B1

(12) United States Patent
Segers et al.

(10) Patent No.: US 6,770,275 B1
(45) Date of Patent: Aug. 3, 2004

(54) LIVE ATTENUATED RTX-PRODUCING BACTERIA OF THE FAMILY PASTEURELLACEAE

(75) Inventors: Ruud Philip Antoon Maria Segers, Boxmeer (NL); Johannes Franciscus Van Den Bosch, Boxmeer (NL); Joachim Frey, Bern (CH)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 08/866,198

(22) Filed: May 30, 1997

(30) Foreign Application Priority Data

May 31, 1996 (EP) .......................................... 96201557

(51) Int. Cl.$^7$ ........................ A01N 63/00; A61K 39/02; A61K 39/116; A61K 39/00
(52) U.S. Cl. ................ 424/93.2; 424/200.1; 424/201.1; 424/203.1; 424/184.1; 424/93.4; 424/236.1; 424/235.1; 424/234.1; 435/245; 435/69.3; 435/71.1; 435/252.3
(58) Field of Search ........................... 424/255.1, 256.1, 424/235.1, 200.1, 201.1, 93.2, 93.48, 203.1, 236.1, 93.4, 234.1, 184.1, 825; 435/71.1, 252.3, 245, 243

(56) References Cited

U.S. PATENT DOCUMENTS

| | | | | |
|---|---|---|---|---|
| 4,963,487 A | * | 10/1990 | Schimmel ................ | 435/172.3 |
| 5,143,830 A | * | 9/1992 | Holland et al. ............ | 435/69.7 |
| 5,165,924 A | | 11/1992 | Shewen et al. ................ | 424/88 |
| 5,256,415 A | | 10/1993 | Corstvet et al. ............... | 424/92 |
| 5,422,110 A | * | 6/1995 | Potter et al. .............. | 424/255.1 |
| 5,733,780 A | * | 3/1998 | Briggs et al. ............. | 135/320.1 |

FOREIGN PATENT DOCUMENTS

| | | | |
|---|---|---|---|
| CA | 2045950 | * | 12/1992 |
| EP | 0400 958 | | 12/1990 |
| WO | WOA 9106653 | | 5/1991 |
| WO | WO 97/16531 | * | 5/1997 |
| WO | WO 97/16532 | * | 5/1997 |

OTHER PUBLICATIONS

CL. Wright et al. Australian Microbiologist 15: p. 30.4, 1994.*
EM. Barry et al. J. Bacteriol. 173: 720–726, 1991.*
D. Gygi et al. Mol. Microbiol. 4: 123–128, 1990.*
TJ. Inzana. Microb. Pathogen. 10: 281–296, 1991.*
JE. MacInnes et al. In: Pathogenesis of Bacterial Infections in Animals, (Eds.) CL Gyles et al., Second Edition, Iowa State University Press, Ames, pp. 188–200, 1993.*
LA. Babiuk et al. Biotech. Adv. 12: 489–523, 1994.*
T. Felmlee et al. Proc. Natl. Acad. Sci. USA. 85: 5269–5273, 1988.*
LA. Pearce et al. Australian Microbiologist 15: p. 30.5, 1994.*
Bhatia et al. Vet. Microbiol. 29: 147–158, 1991.*
Conlon et al. Infect. Immun. 59: 587–591, 1991.*
Frey. Trends Microbiol. 3: 257–261, 1995.*
Forestier et al. Infect. Immun. 58: 828–832, 1990.*
Frey et al. In: Bacterial Protein Toxins, (Ed) Freer et al., Sixth European Workshop, Stirling, Jun. 27–Jul. 2, 1993, FEMS Symposium No. 73, Gustav Fischer Verlag, New York, pp. 322–332, 1994.*
Cruz et al. Mol. Microbiol. 4: 1933–1939, 1990.*
Frey J. Res. Microbiol. 143: 263–269, 1992.*
MacInnes et al. Can. Vet. J. 29: 572–574, 1988.*
Chidambaram et al. Infect. Immun. 63: 1027–1032, 1995.*
Stradhee and Lo. J. Bacteriol. 171: 916–928, 1989.*
Hardie et al. Mol. Microbiol. 5: 1669–1679, 1991.*
Burrows et al. Infect. Immun. 60: 2166–2173, 1992.*
Jansen et al. Infect. Immun. 60: 630–636, 1992.*
Jansen et al. Infect. Immun. 63: 27–37, 1995.*
Devenish et al. Infect. Immun. 57: 3210–3213, 1989.*
Highlander et al. J. Bacteriol. 172: 2343–2350, 1990.*
Tacson et al. J. Bacteriol. 175: 5717–5722, 1993.*
Confer et al. Am. J. Vet. Res. 46: 342–347, 1985.*
Harland et al. Can. Vet. J. 33: 734–741, 1992.*
Betsou et al. Infect. Immun. 61: 3583–3589, 1993.*
Issartel et al. Nature 351: 759–761, 1991.*
Homchampa et al. Vet. Microbiol. 42: 35–44, 1994.*
Boehm et al. Infect. Immun. 58: 1959–1964, 1990.*
Reimer et al., *Microbial Pathogenesis*, 18:197–209, 1995.
V. Braun et al., *Critical Reviews in Microbiology*, 18:2:115–158, 1991.
J. Coote, *FEMS Microbiology Reviews*, 88:2:137–162, 1992.

* cited by examiner

*Primary Examiner*—S. Devi
(74) *Attorney, Agent, or Firm*—William M. Blackstone; William P. Ramey, III (57) ABSTRACT

The present invention relates to live attenuated RTX-toxin producing bacteria of the family Pasteurellaceae, of which the attenuation is due to the fact that they produce RTX toxin in a non-activated form. The invention also relates to vaccines for the protection of mammals against infection with RTX-toxin producing bacteria of the family Pasteurellaceae, and to methods for the preparation of said live attenuated bacteria and vaccines.

7 Claims, 5 Drawing Sheets

LIVE ATTENUATED RTX-PRODUCING BACTERIA OF THE FAMILY PASTEURELLACEAE

FIELD OF THE INVENTION

The present invention relates to live attenuated RTX-producing bacteria of the family Pasteurellaceae, methods for the production of such bacteria, to vaccines comprising such bacteria, methods for the production of such vaccines and methods for the protection of man and animals against infection with virulent RTX-producing bacteria of the family Pasteurellaceae.

BACKGROUND OF THE INVENTION

The family of Pasteurellaceae comprises the genera Haemophilus, Actinobacillus and Pasteurella. The bacteria of this family are also often referred to as bacteria of the HAP-group. Several species of these closely related genera are known to express homologous calcium-dependent, pore-forming cytotoxins, the so-called RTX toxins. (RTX stands for repeat in toxin). RTX toxin-producing bacteria of this family are the cause of a whole range of infectious diseases, influencing both man and animals.

RTX toxins are also known from other genera, not related to the HAP-group, such as Escherichia and Bordetella. These RTX toxins in some respects resemble the RTX-toxins of the HAP-group.

The RTX toxins have been extensively reviewed by Braun et al. (Critical Rev. in Microbiol. 18(2): 115–158 (1991) Gram-negative strains have also been reviewed in Welch, R. A. (Molecular Microbiology 5/3: 521–528 (1991)) and in Welch et al. (Inf. Agents and Disease 4: 254–272 (1995)).

It is the presence of the RTX toxins in the RTX-producing members of the Pasteurellaceae family of bacteria, that highly contributes to the pathogenic character of these bacteria for both man and animals.

All RTX toxins display some kind of cytotoxic or cytolytic activity. The target-cell- and host-specificity differ however, depending on the toxin and on differences in acylation (McWhinney et al.; J. Bact. 174: 291–297 (1992) and Hackett et al.; J. Biol. Chem. 270: 20250–20253 (1995)). As a result of the difference in target cells, the various toxins of the RTX toxin family are known e.g. as haemolysin, cytolysin or cytotoxin.

Although many RTX-producing members of the HAP-group are known, some of them are notorious for the economic damage they cause.

Actinobacillus pleuropneumoniae produces RTX toxins that are cytotoxic/cytolytic to pig, horse, bovine and human erythrocytes, to rabbit and porcine neutrophils and to porcine alveolar macrophages. (Rosendal et al; Am. J. Vet. Res. 49: 1053–1058 (1988), Maudsley J. R. and Kadis S; Can. J. Microbiol. 32: 801–805 (1986), Frey. J and Nicolet. J; Inf. & Imm. 56:2570–2575 (1988), Bendixon et al; Inf. & Imm. 33: 673–676 (1981), Kamp, E. M. and van Leengoed, L. A. M. G.; J. Clin. Microbiol. 27: 1187–1191 (1989)).

Actinobacillus infection in pigs causes severe economic losses to pig industry, due to acute mortality in young pigs and reduced weight gain in older animals.

The Pasteurella haemolytica RTX toxin activity is mainly directed against neutrophils and monocytes/macrophages from ruminants (Shewen and Wilie; Inf. & Immun. 35, 91–94 (1982), Baluyut et al.; Am. J. Vet. Res. 42: 1920–1926 (1981), Himmel et al.; Am. J. Vet. Res. 43: 764–767 (1982)).

Pasteurella infections cause severe problems in ruminants, especially cattle and sheep.

Mastitis and pneumonia are seen in both sheep and cattle, whereas Shipping Fever causes additional problems in cattle. Economic losses due to Pasteurella infections are high. Other, non-HAP-group bacteria are also known to produce RTX toxins.

The E. coli haemolysin is toxic for a large variety of cells, from a large number of different animal species. It lyses erythrocytes from many animal species within a few minutes after contact. (Cavalieri, S. J. and Snyder, I. S.; Inf. & Imm. 37: 966–974 (1982), Gadeberg et al; Inf. & Imm. 41: 358–364 (1983), Keane et al; Am. J. Pathol. 126:305–357 (1987), Bhadki et al; J. Exp. Med. 169: 737–754 (1989)).

The Bordetella pertussis haemolysin also displays a large host-cell range. (Shattuck, R. L. and Storm, D. R.; Biochemistry 24: 6323–6328 (1985), Hewlett et al, In Protein Bacterial Toxins, Rappuoli, R. et al. (Eds), Stuttgart, Fisher-Verlag 249–257 (1990)).

The genetic organisation of the operons involved in the synthesis, activation and transportation of the RTX toxins in Gram-negative bacteria has been reviewed recently by Coote, J. G. (FEMS Microbiology reviews 88: 137–162 (1992)) In general, the RTX operon contains four genes: the actual Toxin gene (A), an Activator gene (C), and two genes (B and D (and E in Bordetella pertussis)) encoding proteins involved in secretion of the toxin into the surrounding medium. The primary translation product of the Toxin-gene (A) is a non-toxic protein.

The role of the Activator gene (C) is of paramount importance in that the gene product encoded by this gene activates the toxic activity of the RTX toxin by posttranslational modification.

This activation results in a structural modification of the toxin. In e.g. Bordetella pertussis, the posttranslational no modification of the RTX toxin is caused by amide-linked palmitoylation of a lysine residue (Hackett et al.; Science 266: 433–435 (1994). The RTX toxin of E. coli could be activated in vitro by transfer of a fatty acyl group from acyl carrier protein to prohaemolysin (Issartel et al.; Nature 351: 759–761 (1991)).

It is known (see e.g. Coote, J. G.; FEMS Microbiology reviews 88: 137–162 (1992)), that RTX toxins are important virulence factors in bacteria belonging to the Pasteurellaceae. This has been shown for e.g. Actinobacillus pleuropneumoniae by Tascon et al.(Mol. Microbiol. 14: 207–216 (1994)) and by Jansen et al. (Inf. & Imm. 63: 27–37 (1995)).

Virulence factors are known to be the main targets for incorporation in vaccines.

Therefore, several attempts have been made to use RTX toxins as subunit vaccines.

In vivo synthesised RTX toxins of the HAP-group are per se produced in the presence of the RTX Activator protein. Therefore, RTX toxins are always posttranslationally modified into highly toxic proteins.

Given their high toxicity it is clear that the RTX toxins need to be detoxified before they can be used as a vaccine component.

Subunit vaccines based on in vivo synthesised RTX toxins from A. pleuropneumoniae that lost their toxicity have been described earlier, e.g. in European Patent EP No. 0.354.628, in which subunit vaccines based upon a haemolysin and a cytotoxin of A. pleuropneumoniae are disclosed, and in European Patent EP No 0.453.024, in which A. pleuropneumoniae subunit vaccines based upon haemolysins, cytotoxins and outer membrane proteins are disclosed.

Subunit vaccines based on RTX toxins from Pasteurella haemolytica have also been disclosed, e.g. in U.S. Pat. No. 5,055,400, Canadian Pat. Appl. CA 2,014,033 and Canadian Pat. Appl. CA 2,081,950.

RTX toxins as subunits for use in vaccines are easily obtained from the supernatant of bacterial cultures of the wild-type strains. Another way of obtaining the RTX toxin as a subunit has been proposed in Canadian Patent Application CA 2,045,950, in which heterologous expression of the genes encoding the *A. pleuropneumoniae* RTX-protein in the heterologous bacterial strain *E. coli* has been described. No vaccine experiments with the RTX toxins so obtained were shown however.

A comparable approach for the production of subunit vaccines has been proposed in European Patent EP 0.500.736. In this patent, the sequence of the RTX Toxin gene (A) and an Activator gene (C), is disclosed. Also a heterologous expression system for the expression of the Toxin gene A in the presence or absence of the Activator gene C is disclosed. No vaccination experiments with the toxin subunit were however, described.

There are however, three important disadvantages to all RTX toxin subunit vaccines:
high amounts of antigenic material are needed in order to adequately trigger the immune system.
usually, only B-cell immunity is triggered.
a live pathogenic bacterium has many important immunogenic molecules, such as Outer Membrane Proteins and capsular polysaccharides, all being important for protection. Therefore, in order to produce an efficient subunit vaccine, one must additionally include as many other immunogenically important antigens as possible.

Next to the obvious problems mentioned under points one and two, especially the third point makes it difficult to make an efficient subunit vaccine.

This is e.g. illustrated by the *A. pleuropneumoniae* subunit vaccine disclosed in European Patent EP No 0.453.024 mentioned above, in which four different subunits (three RTX toxins and an outer membrane protein) are combined in one vaccine.

It is clear that in order to overcome the disadvantages of subunit vaccines against Pasteurellaceae infection, a live attenuated vaccine would be highly desirable.

A live attenuated vaccine has the following advantages:
it can be administered in low doses (it is self-replicating)
it closely mimics the natural/wild-type infection
it provides all the possible immunologically important antigens at the same time.

Nevertheless, in spite of the clear advantages, live vaccines based on bacteria of the HAP-group producing a less active RTX toxin were not available prior to the present invention. The reason for the lack of live attenuated vaccines is clearly illustrated by the following paradox:
The first characteristic of a live attenuated vaccine strain is that it should not produce active RTX toxin, since as mentioned above, it is this RTX toxin that makes strains of the HAP-group so virulent.
A live attenuated bacterium attenuated through the inability to express RTX toxins would, however, per se lack the most important virulence factor i.e. the RTX toxins, and will therefore not trigger an immune response against this toxin.

As a consequence, if the RTX gene(s) is (are) deleted from strains of the HAP-group and such attenuated strains are used as a basis for a vaccine against diseases caused by virulent wild-type strains of the HAP-group, only partial protection is achieved: one would never obtain protective immunity against the most important virulence factor of these wild-type strains i.e. the RTX toxin.

Therefore, vaccines based on bacteria with a deletion of the RTX toxin cannot possibly be expected to provide protection against the damaging effects of the RTX-toxin after infection with wild-type strains.

Strains lacking the apxI operon were made i.a. by Reimer et al. (Microbial Pathog. 18: 197–209 (1995)), who deleted all genes playing a role in the synthesis and transportation of *A. pleuropneumoniae* ApxI Toxin.

Such strains are non-virulent as expected, since they do no longer excrete the most important virulence factor the RTX toxin; but as a consequence no antibodies, let alone protective antibodies, will be induced against the RTX toxins.

SUMMARY OF THE INVENTION

The present application for the first time provides live attenuated RTX toxin-producing bacteria of the family Pasteurellaceae, that do produce the RTX-A toxin, but in a non-activated form.

These bacteria have as a remarkable feature that they are on the one hand attenuated, whereas on the other hand, they are still capable of producing the RTX toxin.

This is achieved by modifying the bacteria in such a way that they do not produce a functional RTX activator protein. Expression of the RTX-A toxin, however, is not impaired.

The advantage of live attenuated strains according to the present invention over subunit vaccines as well as over live strains from which the RTX toxin genes are deleted is that:
they do produce the RTX toxin so that protective antibodies against this toxin are induced
they nevertheless are attenuated in their virulence since they produce the RTX toxin in a non-toxic form
they additionally possess all the other antigens that next to the RTX toxin are necessary to obtain an efficient immune response.

DETAILED DESCRIPTION OF THE INVENTION

RTX-A toxin in a non-activated form is considered to be non-toxic, i.e. not having the same toxic effect as the activated toxin. As mentioned above, this is achieved by modifying the bacteria in such a way that they do not produce a functional RTX activator protein. Expression of the RTX-A toxin, however, is not impaired.

A functional RTX activator protein is considered to be a protein that has all the characteristics of the RTX activator protein as expressed in a wild-type bacterium, and is expressed at the wild-type level.

Therefore, a non-functional RTX activator protein is considered to be a protein that lacks some or all of the characteristics of the RTX activator protein as expressed in a wild-type bacterium, and/or is expressed at a level, insufficient to obtain wild-type levels of activated RTX toxin.

The following must be stressed here: if the non-functional RTX activator protein lacks all of the characteristics of the RTX activator protein as expressed in a wild-type bacterium, the bacterium will produce no activated RTX toxin at all. If however the non-functional RTX activator protein only lacks some of the characteristics of the RTX-activator protein as expressed in a wild-type bacterium, the bacterium may produce part of the RTX toxin in an activated form and part of the RTX toxin in a non-activated form. This is e.g. the case if due to a mutation the Activator protein is expressed, but the activation efficiency of the Activator protein is reduced. The activation speed is the speed with which the Activator protein activates the RTX toxin, i.e. converts the RTX toxin from its non-activated form to its activated form.

It thus goes without saying that bacteria that produce part of the RTX toxin in a non-activated form and part in an activated form are also embodied in the present invention.

Inability to obtain wild-type levels of activated RTX toxin may be the result of a decreased activity of the RTX activator protein. It may also be the result of a decreased expression level of the RTX activator protein, or a combination of the two possibilities.

As a consequence, RTX activator proteins with a decreased activity and/or a decreased expression level are within the scope of the invention.

Alternatively, it is possible to modify the target-site of the RTX Activator protein, i.e. the acylation-site at the RTX-toxin. If this site is modified to the extent that acylation is decreased or absent, this also results in the production of an RTX-toxin in a non-activated form. The acylation site can easily be mutated using recombinant DNA techniques. Mutation can e.g. be obtained by deletion of a restriction fragment that comprises the acylation site, or by site-directed mutagenesis of the acylation site.

A live attenuated bacterium with a non-functional RTX activator protein can be obtained in several ways. One possibility is to introduce a mutation into the gene encoding the RTX-activator protein, preferably by utilising recombinant DNA techniques.

A mutation is understood to be a change of the genetic information in the above-mentioned region with respect to the genetic information present in this region of the genome of the wild-type bacterium. The mutation is, for example, a nucleic acid substitution, deletion, insertion or inversion, or a combination thereof resulting in a bacterium which fails to produce a functional RTX activator protein.

Much is currently known about the location, restriction pattern and often even the nucleotide sequence of the RTX activator genes of RTX toxin producing strains of the HAP-group. This information can e.g. be found in the review by Coote, J. G. (FEMS Microbiology reviews 88: 137–162 (1992)), who gives an overview of structural and functional relationship between the various RTX toxins. Very detailed information about specific RTX toxins can be found in e.g. U.S. Pat. No. 5,055,400, that refers to the RTX-gene of Pasteurella haemolytica, and in Frey et al.; J. Gen. Microbiol. 139: 1723–1728 (1993) and Frey et al.; Proceedings of the HAP-conference U.K., Edinburgh 1994, concerning all genes playing a role in the synthesis and transportation of A. pleuropneumoniae RTX toxins.

Mutation of the gene encoding the RTX activator protein or of sequences involved in the transcription/translation of that gene can be obtained in several ways. One possibility is cloning of the relevant sequences of the RTX activator gene in a vector, excision of part or all of the RTX sequences using restriction enzymes and replacement of the wild-type RTX toxin gene with the mutated sequences. Such a replacement is e.g. performed by the well-known technique of homologous recombination.

Another possibility is the use of site-directed mutagenesis, to obtain the desired mutation.

These standard recombinant DNA techniques are described e.g. by Sambrook et al. in Molecular Cloning: a laboratory manual Cold Spring Harbor Laboratory Press (1989)

Thus, in a preferred embodiment, the bacterium has a mutation in the gene encoding the RTX-activator protein. This mutation may lead to a less active or fully inactive RTX-activator protein depending on the size and character of the mutation.

In a more preferred form, the mutation in the gene encoding the RTX activator protein is a deletion. The deletion may vary highly in size: it may e.g. be as small as one nucleotide, causing frame-shift. On the other hand, the whole gene encoding the RTX activator protein may be deleted.

Another possibility is to leave the gene encoding the RTX-activator protein intact, but to decrease the expression level of the RTX activator protein.

Since the Toxin gene and the Activator gene are transcribed from the same promoter in a polycistronic messenger RNA, it is not possible to decrease the transcription level without concomitantly decreasing the level of expression of the RTX toxin.

However, modification of the expression level of the RTX activator protein can be achieved by introducing a mutation into the ribosome binding site upstream of the gene encoding the RTX activator protein, preferably by utilising recombinant DNA techniques.

Therefore, in another preferred embodiment, the bacterium has a mutation in the region controlling the translation of the RTX activator mRNA, such as the ribosome binding site. Such a mutation influences the efficiency of translation of the RNA encoding the RTX activator protein.

Ribosome binding sites are in general easily detected on the basis of their consensus-motive and the relative distance of about 5–6 nucleotides between the ribosome binding site and the start codon. In many cases, e.g. for several RTX activator genes of A. pleuropneumoniae they are published (Frey et al. Gene 142: 97–102 (1994)).

In a more preferred form of this embodiment, the mutation in the region controlling the translation of the RTX activator mRNA is a deletion. The deletion may e.g. comprise a deletion of one or more nucleotides of the ribosome binding site.

Still another possibility to obtain a live attenuated bacterium with a non-functional RTX activator protein is to add a nucleic acid sequence that codes for an antisense RNA, that can bind to the messenger RNA encoding the Activator protein. Expression of such a sequence then leads to a decrease in the level of activator protein.

Antisense RNA is RNA that has a sequence that is partially or fully complementary to the sequence of the messenger RNA (mRNA) to which it is antisense.

In the most preferred embodiment, the live attenuated bacterium according to the present invention is Actinobacillus pleuropneumoniae.

The present invention also relates to vaccines for the protection of animals against infection with an RTX toxin producing bacterium of the family Pasteurellaceae.

Such vaccines are based on a live attenuated RTX toxin producing bacterium according to the invention and a pharmaceutically acceptable carrier.

These vaccines comprise at least an immunogenically effective amount of the live attenuated RTX toxin producing bacterium according to the invention. Immunogenically effective means that the amount of live attenuated RTX toxin producing bacterium administered at vaccination is sufficient to induce in the host an effective immune response to virulent forms of the RTX toxin producing bacterium.

The useful dosage to be administered will vary depending on the age, weight and mammal vaccinated, the mode of administration and the type of pathogen against which vaccination is sought.

The vaccine may comprise any dose of bacteria, sufficient to evoke an immune response. Doses ranging between $10^3$ and $10^{10}$ bacteria are e.g. very suitable doses.

In addition to an immunogenically effective amount of the live attenuated RTX toxin producing bacterium described above, a vaccine according to the present invention also contains a pharmaceutically acceptable carrier.

Such a carrier may be as simple as water, but it may e.g. also comprise culture fluid in which the bacteria were cultured. Another suitable carrier is e.g. a solution of physiological salt concentration.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Adjuvantia are non-specific stimulators of the immune system. They enhance the immune response of the host to the invading pathogen. Examples of adjuvantia known in the art are Freunds Complete and Incomplete adjuvans, vitamin E, non-ionic block polymers, muramyldipeptides, ISCOMs (immune stimulating complexes, cf. for instance European Patent EP 109942), Saponins, mineral oil, vegetable oil, and Carbopol (a homopolymer).

Adjuvantia, specially suitable for mucosal application are e.g. the *E. coli* heat-labile toxin (LT) or Cholera toxin (CT). Other suitable adjuvants are for example aluminium hydroxide, phosphate or oxide, oil-emulsions (e.g. of Bayol F® or Marcol 52®, saponins or vitamin-E solubilisate.

Therefore, in a preferred form, the vaccines according to the present invention comprise an adjuvant.

For administration to animals, the vaccine according to the presentation can be given inter alia intranasally, intradermally, subcutaneously, by aerosol or intramuscularly.

In a more preferred embodiment, the vaccine according to the present invention additionally comprises one or more antigens selected from other pathogenic microorganisms or viruses. Such a vaccine can be obtained by adding one or more antigens selected from other pathogenic bacteria or viruses to the live attenuated RTX toxin producing bacterium according to the invention and a pharmaceutically acceptable carrier as described above.

Of course, it is possible to add not only one or more antigens, but also one or more of the whole pathogens as such, in an inactivated or live form.

It can alternatively be obtained by cloning the genetic information encoding one or more antigens selected from other pathogenic microorganisms or viruses into the live attenuated RTX toxin producing bacterium, using known recombinant DNA technology. Bacteria according to the present invention are very suitable as carriers, i.e. vectors, for such genetic information, due to their attenuated character. Vaccines based on bacteria according to the present invention that additionally carry genetic information encoding one or more antigens selected from other pathogenic microorganisms or viruses are capable of immunising against two or more diseases at the same time. This is of course less stressing for the animal to be vaccinated than separate vaccinations with each of the pathogens, both from a medical and a physical point of view.

In an even more preferred embodiment, the vaccine according to the present invention comprises live attenuated RTX toxin producing bacterium belonging to the species *Actinobacillus pleuropneumoniae*.

In a still even more preferred form, these antigens are selected from, but not limited, to the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Escherichia coli, Erysipelothrix rhusiopathiae, Pasteurella multocida, Bordetella bronchiseptica, Haemophilus parasuis* and *Streptococcus suis*.

In another form of the even more preferred embodiment, the vaccine according to the present invention comprises live attenuated RTX-toxin producing bacterium belonging to the species *Pasteurella haemolytica*.

In a still even more preferred form of this embodiment, the antigens selected from other pathogenic microorganisms or viruses are chosen from the group of cattle pathogens, consisting of Bovine Rotavirus, Bovine Viral Diarrhoea virus, Parainfluenza type 3 virus, Bovine Paramyxovirus, Foot and Mouth Disease virus, *Pasteurella multocida, Haemophilus somnus, Brucella abortus, Staphylococcus aureus,* Streptococcus spp., Mycoplasma spp., and Bovine Respiratory Syncytial Virus.

There are several ways to store live organisms. Storage in a refrigerator is e.g. a well-known method. Also often used is storage at −70° C. in a buffer containing glycerol. Bacteria can also be kept in liquid nitrogen. Freeze-drying is another way of conservation. Freeze-dried bacteria can be stored and kept viable for many years. Storage temperatures for freeze-dried bacteria may well be above zero degrees, without being detrimental to the viability.

Freeze-drying can be done according to all well-known standard freeze-drying procedures. Optional beneficial additives, such as e.g. skimmed milk, trehalose, gelatin or bovine serum albumin can be added in the freeze-drying process.

Therefore, in a preferred embodiment, the vaccine is in a freeze-dried form.

The invention also refers to the use of vaccines according to the present invention for the protection of susceptible animals against infection with bacteria of the family Pasteurellaceae.

In a preferred embodiment, vaccines according to the present invention are used for the protection of a susceptible animal against *Actinobacillus pleuropneumoniae* infection.

Also, the present invention relates to methods for the preparation of live attenuated RTX toxin producing bacteria of the family Pasteurellaceae.

Said methods comprise the introduction of a mutation in the gene encoding the RTX activator protein.

In a preferred embodiment of this method, the mutation to be introduced is a deletion in the RTX activator protein gene.

Finally, the present invention relates to methods for the preparation of a vaccine for the protection of animals against infection with an RTX toxin producing bacterium of the family Pasteurellaceae. One method comprises admixing bacteria according to the present invention with a pharmaceutically acceptable carrier as described above.

EXAMPLES

Example 1

Preparation of a Live Attenuated *Actinobacillus pleuropneumoniae* Strain

Construction of pApxI-D11

The feasibility of live attenuated bacteria according to the present invention is exemplified by the construction of an *Actinobacillus pleuropneumoniae* ΔapxIC mutant.

In order to obtain this mutant, first a plasmid comprising a deletion in the RTX-Activator gene was made.

Figure 1:
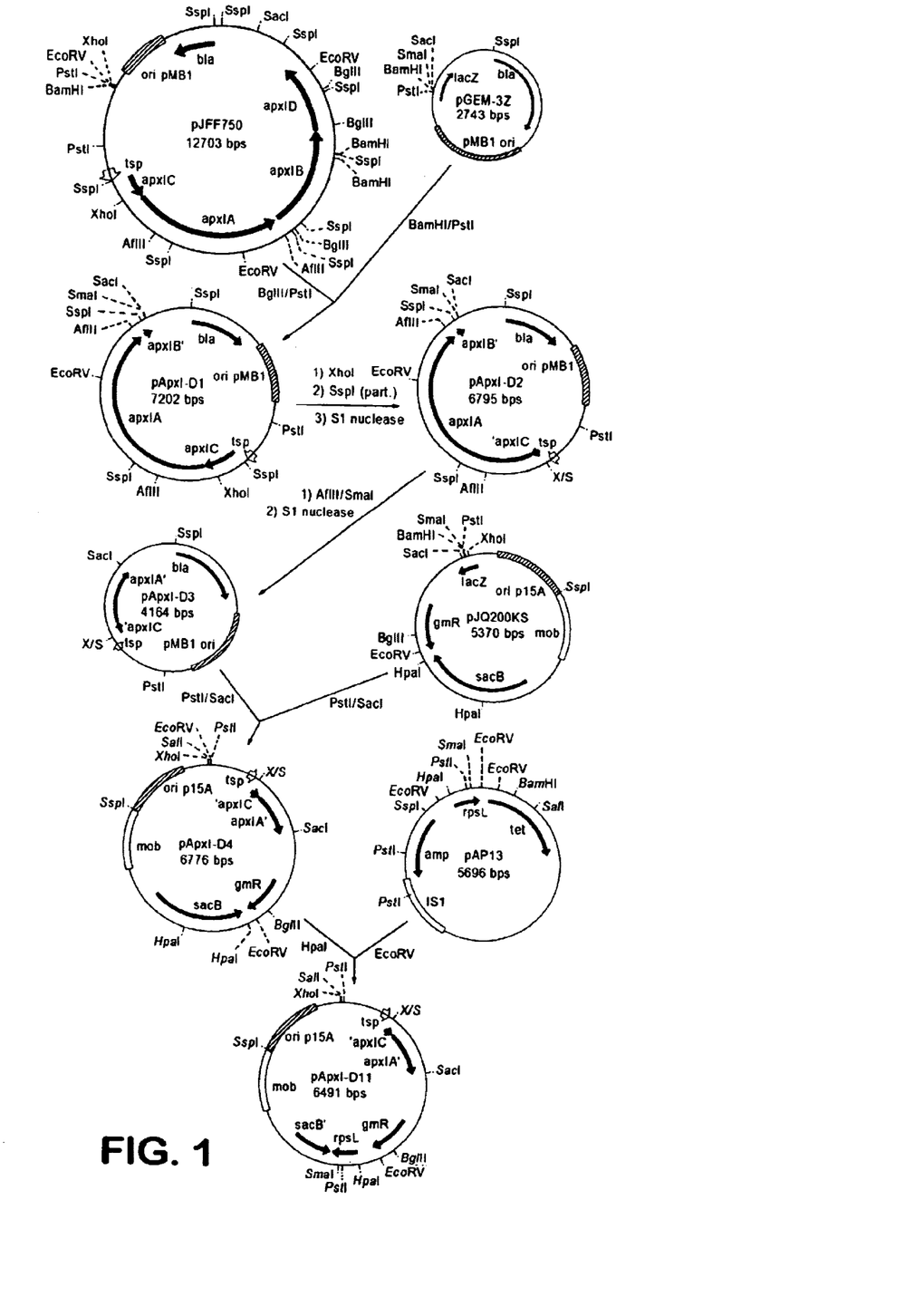
FIG. 1: Construction of pApxI-D11 (see for explanation in the text). The major genetic features of the plasmids used are indicated as well as all restriction sites used. The site where the former XhoI and SspI restriction sites were joined is indicated as "X/S", the transcription starting point of the ApxI operon, as determined by Frey et al., Gene 142;97–102 (1994), is indicated as "tsp".
Figure 2A:
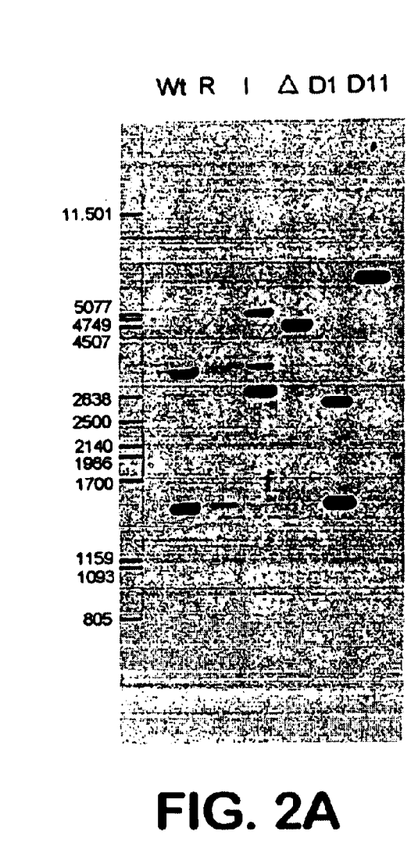
Figure 2B:
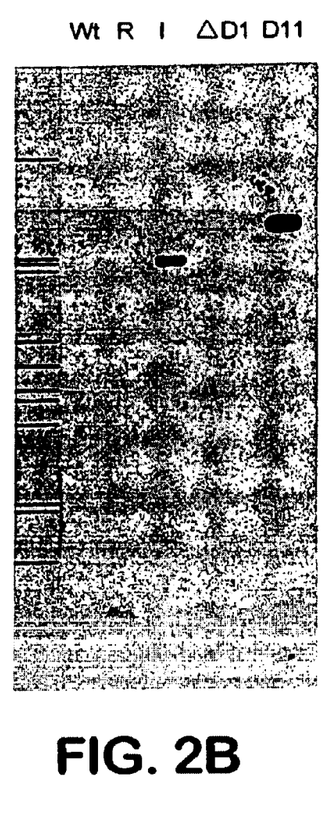
Figure 2C:
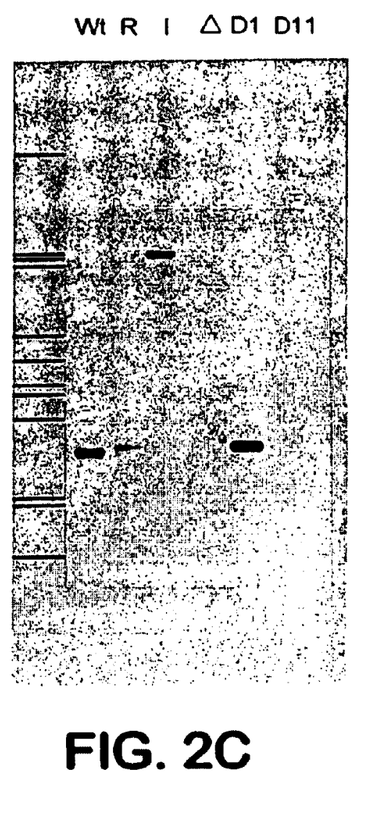
Figure 3:
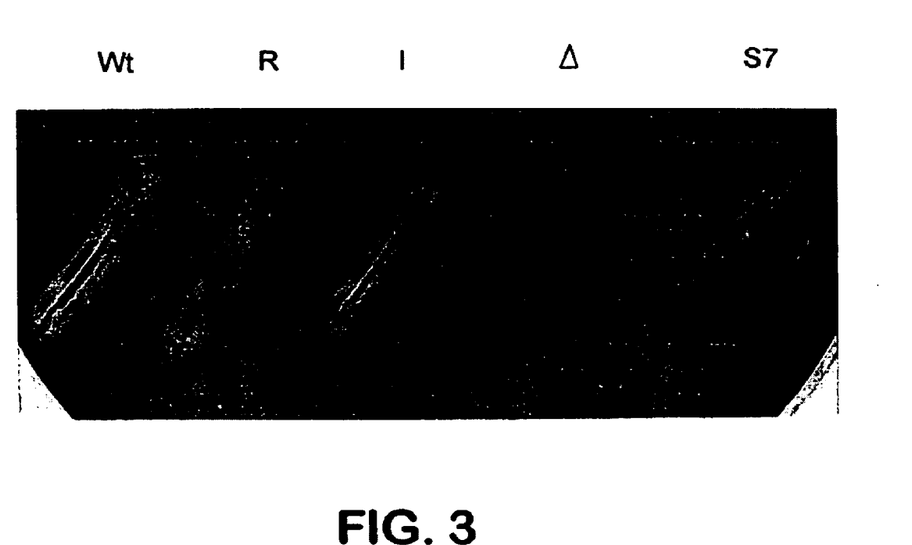
FIG. 3: Haemolysin plate assay. Various strains were picked with a sterile toothpick on a Columbia agar plate containing 0.1% NAD and 2% sheep red blood cells. The plate was subsequently incubated for 8 hours at 37° C. From left to right, the wild-type HV211 strain (Wt), the naladixic acid and streptomycin resistant strain MBHPP105 (R), the insertion mutant (I), the deletion mutant MBHPP113 (D), and the A. pleuropneumoniae serotype 7 reference strain were inoculated.
Figure 4A:
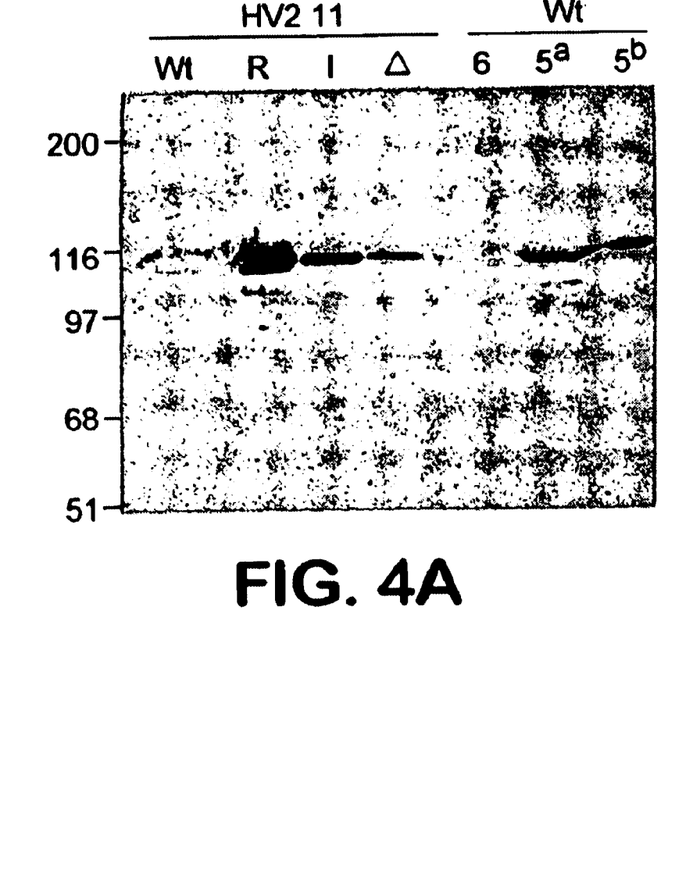
FIGS. 4A and B: Expression of ApxIA and ApxIIA. Concentrated culture supernatants were electrophoresed in parallel polyacrylamide gels and electroblotted onto Immobilon-P. The resulting blots were reacted with monospecific anti-ApxIA serum in FIG. 4A, and with monospecific anti-ApxIIA serum in FIG. 4B. The strains tested are HV211 (WT), MBHPP105 (R), the plasmid integration mutant (I), MBHPP113 (D) and wild-type reference strains of serotypes 6, 5a and 5b. Wild-type reference strain of serotype 6 produces ApxIIA, but not ApxIA.
Figure 4B:
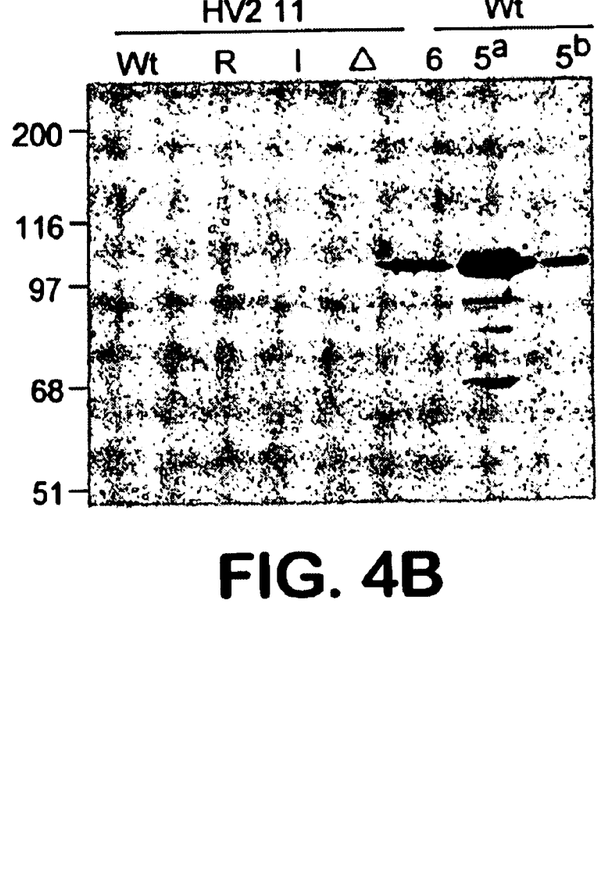

The outline of the construction is given in FIG. 1. The sequence of the apxI operon of *A. pleuropneumoniae* has been deposited in GenBank with accession number X52899. From pJFF750 (Gygi et al.; Infect. Immun. 60:3059–3064, 1992), the apxIC and apxIA genes and the promoter region were excised as a 4481 bp BglII/PstI fragment and cloned into plasmid pGEM3Z (Promega Co., Leiden NL), digested with the enzymes BamHI and PstI. The resulting plasmid was designated pApxI-D1. A 407 bp DNA fragment comprising most of the ApxIC encoding region was excised by digestion with restriction enzyme XhoI, followed by partial digestion with restriction enzyme SspI. The sticky-end overhangs were converted to blunt-ends with S1-nuclease and a fragment of approximately 6800 bp was isolated from agarose gel and religated. The resulting plasmid was designated pApxI-D2. The sequence across the XhoI/SspI deletion junction was verified by nucleotide sequence analysis. Subsequently, most of the ApxIA encoding region was deleted by AflII/SmaI digestion, S1-nuclease blunting and religation. The 1454 bp exchange cassette for allelic replacement was excised from pApxI-D3 with restriction enzymes PstI and SacI and cloned in vector pJQ200KS (Quandt et al.; Gene 127:15–21, 1993), digested with the same enzymes. The resulting plasmid was designated pApxI-D4. The 3' end of the sacB gene in pApxI-D4 was removed by HpaI digestion and replaced by the rpsL gene excised from pAP13 (Prentki et al.; Gene 103:17–23, 1991) as a 540 bp EcoRV fragment. The resulting plasmid was named pApxI-D11.

Results

The structure of the resulting plasmid pApxI-D11 was checked by digestion with various restriction enzymes. The digestion patterns showed, that indeed the desired plasmid was obtained. This plasmid was further used for the construction of an ΔapxIC mutant.

Construction of the ΔapxIC Mutant from *Actinobacillus pleuropneumoniae* Strain HV211

Plasmid pApxI-D11 was used for allelic replacement. To this end it was introduced in *A. Pleuropneumoniae* by conjugation from *E. coli* by standard filter mating technique (De Lorenzo and Timmis, Methods Enzymol. 235:386–405, 1994). The *E. coli* donor, designated MBHPP101 was constructed by transformation of strain SM10 λpir (Miller and Mekalanos, J. Bacteriol. 170:2575–2583 1988) with plasmid pApxI-D11. The *A. pleuropneumoniae* acceptor strain MBHPP105 was isolated after cultivation of the serotype 10 field isolate HV211 (one of the strains tested by Beck et al., J. Clin. Microbiol. 32:2749–2754, 1994) in the presence of streptomycin and subsequently in the presence of both streptomycin and naladixic acid (Strain R). After conjugation, a naladixic acid and gentamycin resistant *A. pleuropneumoniae* exconjugant was obtained after selection on solid media.

The resulting strain (I) contained the pApxI-D11 DNA both as circular plasmid and integrated into the ApxI operon, as judged from analysis by Southern blot. This can be seen in FIG. 2A, where DNA of the indicated strains was hybridised to the 1.478 kB SalI/SacI fragment from pApxI-D11. After further cultivation in the presence of naladixic acid, the strain was plated on blood agar with naladixic acid and an *A. pleuropneumoniae* colony without a haemolytic zone was identified.

Results

This resulting strain, designated MBHPP113, was confirmed to be an ApxIC negative mutant of *A. pleuropneumoniae* serotype 10 by Southern blot analysis (see FIGS. 2A–C). As expected, in SspI digested chromosomal DNA of strain MBHPP113, only one band hybridises with the probe flanking the deleted region (FIG. 2A). The size of the band (approximately 4.4 kB) corresponds to the combined sizes of the two hybridising bands in the chromosomal DNA of the parent strain, minus the 407 bp deletion.

Furthermore, it was shown that the plasmid backbone is no longer present in MBHPP113 (FIG. 2B).

Most importantly, it was shown that the SspI/XhoI fragment comprising the apxIC gene is no longer present in MBHPP113 (FIG. 2C).

Example 2

Tests on expression, excretion and lack of haemolytic activity of RTX-toxin of the ΔapxIC mutant MBHPP113.

Lack of Haemolytic Activity of the *A. pleuropneumoniae* ΔapxIC Mutant MBHPP113

In order to demonstrate the effect of the ΔapxIC deletion in MBHPP113, the haemolytic activities of the ΔapxIC strain MBHPP113 and the wild-type parent strain were compared after growth on a blood plate.

The *A. pleuropneumoniae* reference strain belonging to serotype 7 (only producing ApxII) was also included for comparison. This strain shows an intermediate haemolysis level due to the fact that ApxII has a moderate haemolytic activity.

Individual colonies were transferred to a Columbia agar plate with 0.1% NAD and 2% sheep red blood cells with a sterile tooth pick.

Results

As can be seen from FIG. 3, after 8 hrs of growth at 37° C., the HV211 (Wild-type), MBHPP105 (R, i.e. the resistant strain) and the plasmid integration mutant (I) are surrounded by a haemolytic zone as expected.

The *A. pleuropneumoniae* reference strain for serotype 7 (only producing ApxII) shows an intermediate level of haemolysis. Also as expected, no haemolytic zone could be detected around the ΔapxIC strain MBHPP113 (depicted as Δ in FIG. 3).

This experiment clearly shows, that the ΔapxIC strain MBHPP113 indeed produces no activated Apx-toxin.

Expression and Excretion of apxIA by ΔapxIC Strain MBHPP113

The ΔapxIC strain according to the present invention is supposed to express and excrete an RTX-toxin, but in a non-haemolytic form. Expression and excretion were tested in this experiment.

The excretion of the ApxIA protein was investigated by reaction of concentrated culture supernatant from various *A. pleuropneumoniae* strains with mono-specific anti-ApxIA as described (Beck et al., J. Clin. Microbiol., 32;2749–2754, 1994).

Anti-ApxIIA sera and wild-type strains of other serotypes were used mainly as a comparison.

*A. pleuropneumoniae* was inoculated from chocolate agar plates into 5 ml Columbia Broth medium containing 0.1% NAD, and incubated for 6 hours at 37° C., while shaking at 200 rpm. The cell-free culture supernatants were collected after centrifugation for 30 minutes at 10,000×g. The ApxIA proteins were concentrated 20-fold on a CENTRICON-100 (Millipore Co., Etten-Leur, NL) concentration filter according to the directions of the manufacturer. After electrophoresis on a polyacrylamide gel, the proteins were blotted and reacted with mono-specific anti-ApxIA serum and anti-ApxIIA serum.

Chocolate agar plates contain KH2PO4 (1 g), K2HPO4 (4 g), NaCl (5 g), Proteose peptone No 3 (15 g), starch (1 g), Bacto agar (15 g), sterile water (to 1000 ml total volume), sheep blood (100 ml), horse serum (100 ml) and Isovitalex solution (12 ml).

Results

Concentrated culture supernatants were electrophoresed in parallel polyacrylamide gels and electroblotted onto IMMOBILON-P as depicted in FIG. 4. The resulting blots were reacted with mono-specific anti-ApxIA serum in FIG. 4A, and with mono-specific anti-ApxIIA serum in FIG. 4B. The strains tested are HV211 (Wild-type), MBHPP105 (R, i.e. the resistant strain), the plasmid integration mutant (I), MBHPP113 (Δ) (see under: Construction of the ΔApxIC mutant from *Actinobacillus pleuropneumoniae* strain HV211) and wild-type reference strains of serotypes 6, 5a and 5b. Wild-type reference strain of serotype 6 produces ApxIIA, but not ApxIA.

From the 105 kD-bands in lanes WT, R, I and Δ in FIG. 4A it is clear, that the WT-strain as well as the R-strain, the I-strain and strain MBHPP113 produce and export the ApxIA protein.

The results of the experiments in Example 2 prove, that the *A. pleuropneumoniae* strain MBHPP113 is indeed capable of expressing and exporting the RTX-toxin in a non-activated form.

Example 3
Construction of a ΔapxICΔapxIIC Mutant from *Actinobacillus pleuropneumoniae* Strain 4074

The construction of the ΔapxIC mutation in strain 4074 was performed as described in example 1. The *A. pleuropneumoniae* acceptor strain MBHPP104 was isolated after cultivation of the serotype 1 reference strain 4074 (Frey and Nicolet, J. Clin. Microbiol. 28:232–236, 1990) in the presence of streptomycin and subsequently in the presence of both streptomycin and naladixic acid. After conjugation of MBHPP104 with MBHPP101 (described in example 1), a naladixic acid and gentamycin resistant *A. pleuropneumoniae* exconjugant was obtained. After plating this strain on CBM plates with 2% sheep erythrocytes, 0.1% NAD and naladixic acid, several colonies with a smaller haemolytic zone were identified. One of these, designated MBHPP111, was confirmed to be an apxIC negative mutant of *A. pleuropneumoniae* strain 4074 by Southern blot analysis.

Figure 5:
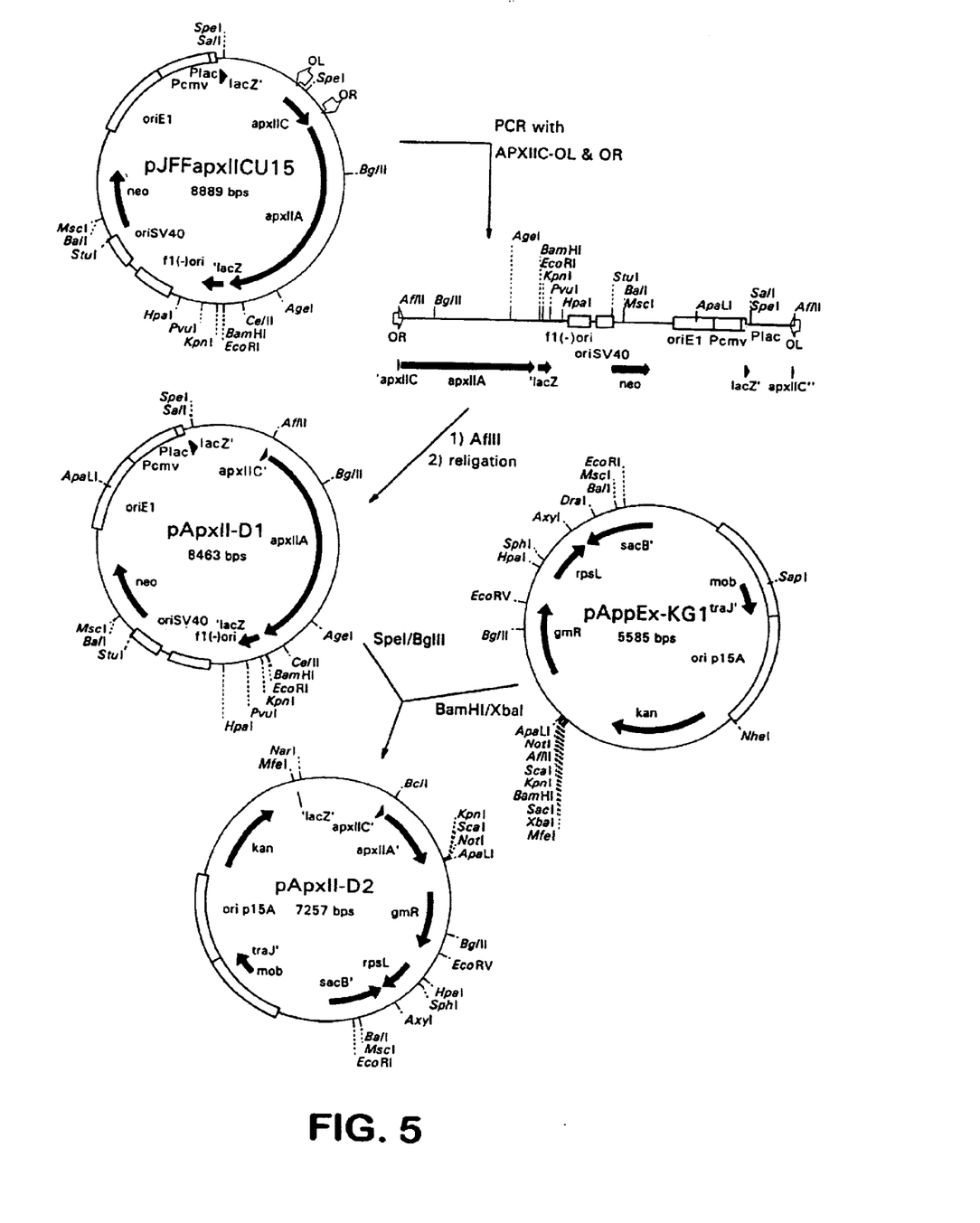
FIG. 5: Construction of pApxII-D2. The major genetic features of the plasmids used are indicated, as well as all restriction sites used.

The apxIIC deletion was made into the MBHPP111 strain in a similar way as the apxIC deletion, using the pApxII-D2 construct (instead of pApxI-D11) in conjugation donor strain MBHPP142. The construction of pApxII-D2 is given in FIG. 5. Briefly, plasmid pJFFapxIICU15 was constructed by insertion of a 4.3 kb fragment containing the apxIIC and apxIIA genes (derived by partial Sau3AI digestion of chromosomal DNA from strain 4074) in vector λZAP Express (Stratagene Co.) and excission using helper phage into vector pBK-CMV (stratagene Co.). An in-frame deletion in the coding region of apxIIC was made by PCR amplification with oligo's APXIIC-OL (5'-CAATACCTTAAGATCATTTTTAGCATCATCCC), SEQ ID 1, and APXIIC-OR (5'-ACATTTCTTAAGTATGAGCAAGAGTTAATAACAGC), SEQ ID 2, using pJFFapxIICU15 as a template. The resulting PCR fragment of 8.5 kb was digested with AflII and religated. The resulting plasmid was designated pApxII-D1 and the sequence across the deletion site was verified by sequence analysis. The insert of pApxII-D1 was excised as a SpeI/BglII fragment and ligated into pAppEX-KGlI digested with XbaI and BamHI. The resulting plasmid was designated pApxII-D2 and transferred to *E. coli* S17-1 λpir (Simon et al., Biotechnology 1;784–791, 1983). This conjugation donor strain was designated MBHPP142.

After conjugation of MBHPP111 with MBHPP142, a naladixic acid and gentamycin resistant. *A. pleuropneumoniae* exconjugant was obtained, which was plated on CBM agar plates containing 0.1% NAD, 2% sheep erythrocytes and 20 μg/ml of Naladixic acid. Non-haemolytic *A. pleuropneumoniae* colonies could be identified. One of them, designated MBHPP147, was confirmed to be an apxIC apxIIC deletion mutant of *A. pleuropneumoniae* strain 4074 by Southern blot analysis.

Results

The construction steps resulted in strain MBHPP147, having deletions in both the apxIC and apxIIC genes.

Haemolytic Activities of the *A. pleuropneumoniae* Serotype 1 ΔapxC Mutants

The haemolytic activities of the ΔapxIC strain MBHPP111, the ΔapxIC ΔapxIIC double deletion mutant MBHPP147, and the wild-type parent strain MBHPP104 were compared after growth on a blood plate (as described in example 2). Individual colonies were transferred to a CBM plate with 0.1% NAD and 2% sheep red blood cells with a sterile tooth pick. After 8 hr growth at 37° C. the wild-type strain MBHPP104 was surrounded by a β-haemolytic zone of 2 mm. The MBHPP111 strain, still producing activated ApxIIA, produced a more diffuse haemolytic zone of approximately 1 mm (comparable to the haemolytic zone surrounding the *A. pleuropneumoniae* reference strain for serotypes 7 and 12, which are known to produce only ApxII). The MBHPP147 double deletion mutant was non-haemolytic.

Results

The apxIC deletion results in loss of the strong haemolytic activity, which is typical for the ApxI hemolysin. The subsequent apxIIC deletion results in complete loss of haemolytic activity. The results are summarised in table 1.

TABLE 1

Summary of haemolysis and Western blot results. The haemolytic zone is indicated in mm and "(d)" indicates diffuse haemolysis. A "+" indicates a reaction in western blot of antibodies with an antigen of approximately 105 kDa. A "–" indicates the absence of such a reaction.

| STRAIN | Haemolytic zone (mm) on blood agar | Western blot reaction anti-ApxIA antibodies | Western blot reaction anti-ApxIIA antibodies |
|---|---|---|---|
| MBHPP104 | 2 | + | + |
| MBHPP111 | 1 (d) | + | + |
| MBHPP147 | 0 | + | + |
| serotype 10 | 2 | + | – |
| serotype 12 | 1 (d) | – | + |

Expression and Excretion of ApxIA and ApxIIA by ΔapxC Strains Derived from Serotype 1 Strain 4074

The excretion of the ApxIA protein was investigated by reaction of concentrated culture supernatant from various *A. pleuropneumoniae* strains with monospecific anti-ApxIA and anti-ApxIIA sera in a Western blot procedure as described (Beck et al., J. Clin. Microbiol., 32;2749–2754, 1994 and example 2).

Results

All serotype 1 strains (MBHPP104, MBHPP111 and MBHPP147) were shown to still express and excrete both ApxIA and ApxIIA. As controls, concentrated supernatants from a serotype 10 strain (expressing only ApxI) and a serotype 12 strain (expressing only ApxII) were included. The results are summarised in table 1.

Example 4

Effect of ΔapxC Mutations on Virulence of *A. pleuropneumoniae* in Mice

To determine the effect of the apxIC and/or apxIIC deletions on the virulence of *A. pleuropneumoniae*, groups of seven mice (between 6 and 7 weeks of age) were challenged by intraperitoneal injection with three different doses of five different strains (see table 2). The strains were freshly grown in CBM medium with 0.1% NAD and washed once with a 0.9% (w/v) NaCl solution and resuspended in the same buffer to an OD600 of 0.8 (representing approximately $3 \cdot 10^9$ cfu/ml). Subsequently, 10 and 100-fold dilutions were made in the same buffer. Each group of mice was intraperitoneally injected with 0.5 ml of one of the dilutions of one of the strains. Serial dilutions of the remainder of the challenge cultures were plated on CBM plates containing 0.1% of NAD and the true cfu content of the challenge cultures was calculated.

Results

From the data it can be concluded that the LD50 of strain HV211 was increased at least 20-fold by the apxIC deletion. For strain 4074, a single ΔapxIC deletion results in a more than 10-fold increase of the LD50. An additional ΔapxIIC mutation results in another 9-fold increase, adding up to a total of at least 90-fold decrease in virulence. The results are given in table 2.

In the control groups all mice died whereas 9 out of 10 vaccinates resisted the homologous challenge with the serotype 1 strain MBHPP104 (p=0.0001 Fisher exact test), and 4 out of 10 vaccinates were protected against heterologous challenge with the serotype 10 strain MBHP105 (p=0.0433 Fisher exact test). Strain MBHPP147 can be used as a live vaccine which confers significant homologous and heterologous protection. The results are shown in table 3.

TABLE 3

Protection of mice after vaccination with MBHPP147 against challenge with virulent serotype 1 (MBHPP104) and serotype 10 strains (MBHPP105).

| Group | Vaccination (at age of 7 weeks) MBHPP147 | Booster Vaccination (at age of 11 weeks) MBHPP147 | Challenge (at age of 13 weeks) | Survival (7 days post challenge) | Significance (p) of protection |
|---|---|---|---|---|---|
| 1 | 1.5 $10^8$ cfu | 1.5 $10^8$ cfu | $10^8$ cfu MBHPP104 | 9 | 0.0001 |
| 2 | — | — | $10^8$ cfu MBHPP104 | 0 | |
| 3 | 1.5 $10^8$ cfu | 1.5 $10^8$ cfu | $10^6$ cfu MBHPP105 | 4 | 0.0433 |
| 4 | — | — | 106 cfu MBHPP105 | 0 | |

TABLE 2

Attenuation of A. pleuropneumoniae by apxC gene deletions. Strain MBHPP105 is the naladixic acid and streptomycin resistant derivative of serotype 10 field isolate HV211; MBHPP113 is an apxIC deletion mutant derived from MBHPP105; MBHPP104 is a naladixic acid and streptomycin resistant derivative of serotype 1 reference strain 4074; MBHPP111 is an apxIC deletion mutant, derived from MBHPP104; MBHPP147 is the apxIC apxIIC double deletion mutant, derived from MBHP111.

| GROUP | STRAIN | DOSE (cfu) | TOTAL DEAD | APPROX. LD50 (cfu) |
|---|---|---|---|---|
| 1 | MBHPP105 | $0.4 \times 10^7$ | 7 | $<0.4 \times 10^7$ |
| 2 | MBHPP105 | $0.4 \times 10^8$ | 7 | |
| 3 | MBHPP105 | $0.4 \times 10^9$ | 7 | |
| 4 | MBHPP113 | $0.7 \times 10^7$ | 0 | $0.8 \times 10^8$ |
| 5 | MBHPP113 | $0.7 \times 10^8$ | 2 | |
| 6 | MBHPP113 | $0.7 \times 10^9$ | 7 | |
| 7 | MBHPP104 | $2 \times 10^7$ | 7 | $<2 \times 10^7$ |
| 8 | MBHPP104 | $2 \times 10^8$ | 7 | |
| 9 | MBHPP104 | $2 \times 10^9$ | 7 | |
| 10 | MBHPP111 | $2 \times 10^7$ | 0 | $2 \times 10^8$ |
| 11 | MBHPP111 | $2 \times 10^8$ | 3 | |
| 12 | MBHPP111 | $2 \times 10^9$ | 7 | |
| 13 | MBHPP147 | $1.8 \times 10^7$ | 0 | $1.8 \times 10^9$ |
| 14 | MBHPP147 | $1.8 \times 10^8$ | 0 | |
| 15 | MBHPP147 | $1.8 \times 10^9$ | 4 | |

Protection of Mice Against A. pleuropneumoniae Challenge, Using Live MBHPP147 as a Vaccine Four groups of 10 mice were used (see table 3). Two groups were vaccinated at 7 weeks of age with an intraperitoneal injection containing 1.5 $10^8$ cells of strain MBHPP147. These mice were boosted with a similar injection 4 weeks later. Two weeks after the booster, one vaccinated and one non-vaccinated group was challenged with an intraperitoneal injection of $10^8$ cfu of strain MBHPP104 (the virulent serotype 1 strain, from which MBHPP147 was derived). The other two groups were challenged with $10^6$ cfu of strain MBHPP105 (a virulent serotype 10 strain).

Results

Legend to the figures:

FIGS. 2A–C: Southern blot analysis of SspI digestions of chromosomal DNA from the HV211 wild-type strain (Wt), the derived streptomycin and naladixic acid resistant strain MBHPP105 (R), the intermediate integration (I) and the final deletion construct MBHPP113 (D). For comparison the plasmids pApxI-D1 (D1) and pApxI-D11 (D11) were included also. In FIG. 2A, the blot was hybridised with the 1.487 kB SalI/SacI fragment from pApxI-D11 (containing the regions flanking the deletion. In FIG. 2B, the blot was hybridised with the pApxI-D11 vector backbone (isolated as a 5004 bp SalI/SacI fragment). In FIG. 2C, the blot was hybridised with a 369 bp fragment (generated by PCR amplification) located within the deleted part of apxIC.

We claim:

1. An isolated live, attenuated Apx toxin-producing *Actinobacillus pleuropneumoniae* having a deletion in two apx activator genes wherein said *Actinobacillus pleuropneumoniae* does not produce two functional Apx activator proteins, but produces two Apx toxins in a non-activated form.

2. A vaccine for the protection of animals against infection by Apx toxin-producing *Actinobacillus pleuropneumoniae* comprising an immunogenically effective amount of the live attenuated *Actinobacillus pleuropneumoniae* according to claim 1 and a pharmaceutically acceptable carrier.

3. The vaccine according to claim 2 wherein said *Actinobacillus pleuropneumoniae* carries said deletion in regions of the genes controlling the translation of the apx activator mRNA.

4. The vaccine according to claim 2, further comprising an adjuvant.

5. The vaccine according to claim 2, which is in freeze-dried form.

6. The vaccine according to claim 1 further comprising one or more antigens selected from the group consisting of Bovine Rotavirus, Bovine Viral Diarrhoea virus, Parainfluenza type 3 virus, Bovine Paramyxovirus, Foot and Mouth Disease virus, *Pasteurella multocida, Haemophilus somnus, Brucella abortus, Staphylococcus aureus,* Streptococcus spp., Mycoplasma spp., and Bovine Respiratory Syncytial Virus.

7. A method for producing an isolated live, attenuated RTX toxin-producing *Actinobacillus pleuropneumoniae* that produces two Apx toxins in a non-activated form, said method comprising introducing a deletion in two apx activator genes whereby said *Actinobacillus pleuropneumoniae* does not produce two functional Apx activator proteins, but produces said two Apx toxins in a non-activated form.

* * * * *

SEQUENCE LISTING

<160> NUMBER OF SEQ ID NOS: 2

<210> SEQ ID NO 1
<211> LENGTH: 33
<212> TYPE: DNA
<213> ORGANISM: Actinobacillus pleuropneumoniae

<400> SEQUENCE: 1
caataccttc agatcatttt ttagcatcat ccc                33

<210> SEQ ID NO 2
<211> LENGTH: 35
<212> TYPE: DNA
<213> ORGANISM: Actinobacillus pleuropneumoniae

<400> SEQUENCE: 2
acatttctta agtatgagca agagttaata acagc              35